US006884777B1

(12) United States Patent
Funanage et al.

(10) Patent No.: US 6,884,777 B1
(45) Date of Patent: \*Apr. 26, 2005

(54) METHOD FOR TREATING RESPIRATORY DISTRESS SYNDROME

(75) Inventors: Vicky L. Funanage, Wilmington, DE (US); Sandra G. Hassink, Wilmington, DE (US); Susan M. Kirwin, Thornton, PA (US); Darlise O'Connor, Newark, DE (US)

(73) Assignee: The Nemours Foundation, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/711,295

(22) Filed: Nov. 14, 2000

(51) Int. Cl.$^7$ .............................................. A61K 38/19

(52) U.S. Cl. ........................................ 514/12; 530/351

(58) Field of Search ............................ 514/12; 530/350, 530/351; 424/422, 434, 450, 185.1; 536/23.5; 435/69.1

(56) References Cited

U.S. PATENT DOCUMENTS

| | | |
|---|---|---|
| 5,773,416 A | 6/1998 | Chehab |
| 5,795,909 A | 8/1998 | Shashoua et al. |
| 5,847,008 A | 12/1998 | Doebber et al. |
| 5,854,067 A | 12/1998 | Newgard et al. |
| 5,859,051 A | 1/1999 | Adams et al. |
| 5,866,341 A | 2/1999 | Spinella et al. |
| 5,891,717 A | 4/1999 | Newgard et al. |
| 5,942,540 A | 8/1999 | Kozachuk |
| 5,962,265 A | 10/1999 | Norris et al. |
| 6,020,382 A | 2/2000 | Doebber et al. |
| 6,022,737 A | 2/2000 | Niven et al. |

OTHER PUBLICATIONS

Torsday et al., FASEB Journal, The roles of parathyroid hormone–related protein (PTHrP) and leptin in type II cell surfactant synthesis. Mar. 15, 2000, vol. 14, No. 4, pp. A782.*
Pelleymounter et al., Science, vol. 269, No. 5223, 1995, pp. 540–543.*
Halliday et al. The OSECT trail. In: Hot Topins in Neonatology. Ross Laboratories, 267–275, 1999.*
O'Donnell et al. Leptin prevents respiratory depression in obesity. AM J. Resp. Crit. Care, 159: 1477–84, 1999.*
Smith–Kirwin et al., Journal of Clinical Endocrinology and Metabolism. Leptin expression in human mammary epithelial cells and breast milk. 83: 1810–1813, May 1998.*
Torsday et al., FASEB Journal, The roles of parathyroid hormone–related protein (PTHrP) and leptin in type II cell surfactant synthesis. Mar. 15, 2000, vol. 14, No. 4, pp. A782.*

Torsday et al., Pediatric Research, Leptin mediates parathyriod hormone–related protein (PTHrP) effects on alveolar differentation and integrity. 378A, Mar. 2000.*
Griese, M. European Respiratory Journal. Pulmonary surfactant in health and human lung diseases: state of the art. vol. 13, pp. 1455–1476, 1999.*
Michael Spear, et al.: "Leptin Values in Bronchopulmonary Dysplasia: Effect of Steroid Use." Pediatric Research, vol. 49, No. 4, Part 2, Apr. 2001, p. 295A; XP009029817; Annual Meeting of the Pediatric Academic Societies, Baltimore, Maryland, USA; Apr. 28–May 1, 2001; ISSN: 0031–3998 (the whole document).
J. Mueleer–Berghaus, et al.: "Leptin in Cystic Fibrosis Patients." Hormone Research (Basel), vol. 48, No. Suppl. 2, 1997, p. 185; XP009029818; 5$^{th}$ Joint Meeting of the European Society for Paediatric Endrocrinology and the Lawson Wilkins Society, Stockholm, Sweden; Jun. 22–26, 1997; ISSN: 0301–0163 (the whole document).
C. G. Tankersley, et al.: "Leptin Attenuates Respiratory Complications Associated with the Obese Phenotype." Journal of Applied Physiology, vol. 85, No. 6, Dec., 1998, pp. 2261–2269; XP002279447; ISSN: 8750–7587 (*p. 2266, col. 1—p. 2268, col. 1*).
Resto et al, "Leptin Levels in Preterm Human Breast Milk and Infant Formula", *Pediatrics* vol. 108 No. 1, pp. 1–4, 2001.
Cinaz et al, "Plasma Leptin Levels of Large for Gestational Age and Small for Gestational Age Infants", *Acta Paeditar,* vol. 88, pp. 753–756, 1999.
Griese et al, Pulmonary Surfactant in Health and Human Lung Diseases: State of the Art, *European Respiratory Journal Ltd,* 13: pp. 1455–1476, 1999.
Rooney et al., "Molecular and Cellular Processing of Lung Surfactant" *The FASEB Journal* vol. 8, pp. 958–967, 1994.
Whitsett et al., "Human Surfactant Protein B: Structure, Function, Regulation, and Genetic Disease" *Physiological Reviews* vol. 75, No. 4, pp. 749–757, 1995.
Spear et al, "Immaturity or Starvation? Longitudinal Study of Leptin Levels in Premature Infants", *Biology of the Neonate* 80 (abstract), 2001, pp. 35–40.

(Continued)

*Primary Examiner*—Lorraine Spector
*Assistant Examiner*—Eileen B. O'Hara
(74) *Attorney, Agent, or Firm*—McGuire Woods LLP

(57) ABSTRACT

The invention provides a method for treating infants, children or adults suffering from pulmonary distress caused by low or insufficient production of surfactant. It is particularly suitable for treating premature infants suffering from Respiratory Distress Syndrome. The method comprises administering a leptin compound to an individual with impaired surfactant production for a time and in an amount sufficient to enhance surfactant production. The method may be used for treatment of any mammal with impaired lung surfactant production.

11 Claims, 6 Drawing Sheets

OTHER PUBLICATIONS

Medelson & Boggaram, "Hormonal and Developmental Regulation of Pulmonary Surfactant Synthesis in Fetal Lung", *Bailliere's Clinical Endocrinology and Metabolism,* vol. 4, No. 2, pp. 351–378, 1990.

Bader, D., Ramos, A.D., Lew, C.D., Platzker, A.C., Stabile, M.W., and Keens, T.G. Childhood sequelae of infant lung disease: exercise and pulmonary function abnormalities after bronchopulmonary dysplasia. J. Pediatr. 110(5):693–9, 1987.

Bado, A., Levasseur, S., Attoub, S., Kermorgant, S., Laigneau, M., Bortoluzzi, M., Moizo., L., Lehy, T., Guerre–Millo, M., Le Marchand–Brustel, Y., and Lewin, M.J.M., The stomach is a source of leptin. Nature 394: 790–3, 1998.

Bhandari, V., Lu, H., Pachter, J., Kresch, M.J. Actin polymerization is developmentally regulated in rat type II cells exposed to terbutaline Pediatr Res 41:166–171, 1997.

Campfield, L.A., Smith, F.J., and Burn, P. Strategies and potential molecular targets for obesity treatment Science 280: 1383–1387, 1998.

Chien, E.K., Hara, M., Rouard, M., Yano, H., Phillippe, M., Polonsky, K.S., and Bill, G.I. Increase in serum leptin and uterine leptin receptor messenger RNA levels during pregnancy in rats. Biochem. Biophys. Res. Comm. 237: 476–480, 1997.

Cioffi, J.A., Shafer, A.W., Zupanic, T.J., Smith–Gbur, J., Platkah, M., Snodgrass, H.R. Novel B219/OB receptor isoforms. Possible role of leptin in hematopoesis and reproduction. Nature Med 2: 585–589, 1996.

Gainsford, T., Wilson, T.A., Metcalf, D., Handman, E., McFarlane, C., Ng, A., Nicola, N.A., Alexander, W.S., and Hilton, D.J. Leptin can induce proliferation differentiation and functional activation of hematopoetic cells. Proc. Natl. Acad. Sci. USA 93: 11564–8, 1996.

Gibson, A.T., Pearse, R.G., Wales, J.K.H. Growth retardation after dexamethasone administration assessment by knemometry, Arch. Dis. Child. 69: 505–9, 1993.

Gibson, R.L., Jackson, J.C., Twiggs, G.A., Redding, G.J., Truog, W.E. Bronchopulmonary dysplasia Survival after prolonged mechanical ventilation. Am. J. Dis. Child. 143(7):721–5, 1988.

Gross, I., and Wilson, C.M. Fetal lung maturation: initiation and modulation. J. Appl. Physiol. 55: 1725–1732, 1983a.

Halliday, HL., Patterson CC. Hatahkoon CN. The OSECT trial. In: Hot Topics in Neomatology. Ross Laboratories, 267–275, 1999.

Hassink, S.G., Sheslow, D.V., deLancey E.M. Opentanova, L., Considine, R.V., and Caro, J.F. Serum leptin in children with obesity: relationship to gender and development. Pediatrics 98: 201–205, 1996.

Hassink, S.G. deLancey, E., Sheshlow, D., Smith–Kirwin,S., O'Connor, D. Considine, R. Opentanova, L., Dostal, K., Spear, M., Leef, K., Ash, M., Spitzer, A., Funanage, V. Placental leptin: an important new growth factori in intrauterine and neonatal development? Pediatrics 100: c1–6, 1997.

Highman, T.J., Friedman, J.E., Huston, L.P., Wong, W.W., and Catalano, P.M. Longitudinal changes in maternal serum leptin concentrations, body composition, and resting metabolic rate in pregnancy. Am. J. Obstet. Gynecol. 178: 1010–5, 1998.

Hoggard, N., Hunter, L., Duncan, J.S., Williams, L., Trayhun, P., Mercer, J.G. Leptin and leptin receptor mRNA and protein expression in the murine fetus and placenta. Proc. Nat. Acad. Sci. 94:1073–1078, 1997.

Jaquet, D., Leger, J., Levy–Marchal, C., Oury, J.F., and Czernichow, P. Ontogeny of leptin in human fetuses and newborns: effect of intrauterine growth retardation on serum leptin concentrations. J. Clin. Endo. Metab. 83: 1243–6, 1998.

Kamohara, S., Burcelin, R., Halaas, J.L., Friedman, J.M., and Charron, M.J. Acute stimulation of glucose metabolism in mice by leptin treatment. Nature 389: 374–7, 1997.

Kurzner, S.L., Garg, M., Bautista, D.B., Bader, D., Merritt, R.J., Warburton, D., and Keens, T.G. Growth failure in infants with bronchopulmonary dysplasia: nutrition and elevated resting metabolic expenditure. Pediatrics 81(3):379–84, 1988.

Liggins, G.C. and Howie, M.B., A controlled trial of antepartum glucocorticoid treatment for prevention of respiratory distress syndrome in premature infants. Pediatrics 50: 515–525, 1972.

Lord, G.M., Matarese, G., Howard, J.K., Baker, R.J., Bloom, S.R., Lechler, R.I. Leptin modulates the T–cell immune response and reverses starvation–induced immunosuppression. Nature 394: 897–901, 1998.

Masuzaki, H., Ogawa, Y., Sagawa, H., Hosada, K., Matsumoto, T., Mise, H., Nishimura, H., Yoshimasa, Y., Tanaka, I., More, T., and Nakao, K.N. Nonadipose tissue production of leptin: leptin as a novel placenta derived hormone in humans. Nature Med. 3:1029–1033, 1997.

Matsuda, J., Yokota, I., Iida, M., Murakami, T., Natio E., Ito, M., Shima, K., and Kuroda, Y. Serum leptin concentration in cord blood: relationship to birthweight and gender. J. Clin. Endo. Metab. 82: 1642–1645, 1997.

Mendelson, C.R. and Boggaram, V. Hormonal and developmental regulation of pulmonary surfactant synthesis in fetal lung. Baillere's Clinical Endocrinology and Metabolism 4: 351–378, 1990.

O'Donnell, C.P., Schaub, C.D. Haines, A.S., Berkowitz, D.E., Tankersley, C.G., Schwartz, A.R., and Smith, R.L. Leptin prevents respiratory depression in obesity. Am. J. Resp. Crit. Care Med. 159: 1477–84, 1999.

O'Shea, T.M., Kothadia, J.M., Klienpeter, K.L., Goldstein, D.J., Jackson, B.G., Weaver, R.G. 3$^{rd}$, and Dillard, R.G. Randomized placebo–controlled trial of a 42–day tapering course of dexamethasone to reduce the duration of ventilator dependency in very low birth weight infants: outcome of study participants at 1–year adjusted age. Pediatrics 104(1 part 1):15–21, 1999.

Pierce, M.R and Bancalari, E. The role of inflammation in the pathogenesis of bronchopulmonary dyplasia. Pediatr. Pulmonol. 19(6):371–8, 1995.

Post, M. and Smith, B.T. Histochemical and immunocytochemical identification of alveolar type II epithelial cells isolated from fetal rat lung. Am. Rev. Respir. Dis. 137: 525–530, 1988.

Rohner–Jeanrenaud, F. and Jeanrenaud, B. Obesity leptin and the brain. N. Engl. J. Med. 334: 324–325, 1996.

Smith–Kirwin. S.M., O'Connor, D.M., Johnston, J., deLancey, E, Hassink, S.G., Funanage, V.L., Leptin expression in human mammary epithelial cells and breast milk. J. Clin. Endocrin. Metab. 83: 1810–1813, 1998.

Soll. R.F., for the Vermont Oxford Network Steriod Study Group. Early postnatal dexamethasone therapy for the prevention of chronic lung disease. Pediatr. Res. 45:226A, 1999.

Stark, A., Carlo, W., Bauer, C., Donovan, E., Oh, W., Papile, L., Shankaran, S., Tyson, J.E., Wright, L.L., Temprosa, M., Poole, K. for the NICHD Neonatal Research Network. Complications of early steroid therapy in a randomized controlled trial. Pediatrics 104:739, 1999.

Tankersley, C.G., O'Donnell, C., Daood, M.J. Watchko, J.F. Mintzer, W., Schwartz, A., Smith, P. Leptin attenuates respiratory complications associated with the obese phenotype. J. Appl. Physiol. 85: 2261–2269, 1998.

Tankersley, C., Kleeberger, S., Russ, B., Schwartz, A., Smith, P. Modified control of breathing in genetically obese(ob/ob) mice J. Appl. Physiol. 81: 716–723, 1996.

Tomimatsui, T., Yamaguchi, M., Mraakami, T., Ogura, K., Sakata, M., Mitsuda, N., Kanzaki, T., Kwack, H., Irahava, M., Miake, A., Shim.a K, Aeno, T., and Murata, Y. Increase of mouse leptin production by adipose tissue after midpregnancy; gestation profile of serum leptin concentration. Biochem. Biophys. Res. Comm. 240: 213–215, 1997.

Torsday, J.S., Sun, H., Ling, W., Torres, E., Leptin mediates parathyroid homone–related protein (PTHrP) effects on alveolar differentation and integrity. Pediatr. Res. 378A, 2000.

Tsai, F.J., Tsai, C.H., Wu, S.F., Liu, Y.H., and Yeh, T.F. Catabolic effect in premature infants with early dexamethasone treatment. Acta Paediatr 85(12):487–90, 1996.

Tsuchiya, T., Shimizu, H., Horie, T., and Mori, M. Expression of leptin receptor in lung: leptin as a growth factor, Exp. J. Pharmacol. 365: 273–279, 1999.

Ur. E. Grossman, A. Despres, J.P., Obesity results as a consequence of glucocortoid induced leptin resistnace. Horm. Metab. Res 28: 744–7, 1996.

Vohr, B.R., Colt, C.G., Lobato, D., Yunis, K.A., O'Dea, C. and Oh, W. Neurodevelopmental and medical status of low–birthweight survivors of bronchopulmonary dysplasia at 10 to 12 years of age. Dev. Med. Chil. Neurol. 33(8):690–7, 1991.

Wang, J., Liu, R., Hawkins, M., Barzilai, N., and Rosetti, L., A nutrient sensing pathway regulates leptin gene expression in muscle and fat. Nature 393: 684–688, 1998.

Wang, J., Liu, R., Liu, L., Chowdhury, R., Barzilai, N., Tani, J., and Rossetti, L., The effect of leptin on Lep expression is tissue–specific and nutritionally regulated. Nature Med. 5: 895–899, 1999.

Yeh, T.F., Lin, Y.J., Huang, C.C., Chen Y.J., Lin, C.H., Hsieh, W.S., and Lien, Y.J. Early dexamethasone therapy in preterm infants, a follow–up study. Pediatrics 101(5):E7, 1998.

Zakrewska, K.E., Cusin, I., Sainsbury, L., Rohrer–Jeanrenaud, F., Jeanrenaud, B., Glucocorticoids as counterregulatory hormones of leptin: toward an understanding of leptin resistance. Diabetes 46: 717–9, 1997.

Zhang, Y., Proenca, R., Maffei, M., Barone, M., Leopold, L., and Friedman, J.M. Positional cloning of the mouse obese gene and its human homologue. Nature 372: 425–432, 1994. (Erratum appears in Nature 374: 47, 1995).

Chehab, F. F., Lim, M. E. & Lu, R., "Correction of the sterility defect in homozygous obese female mice by treatment with the human recombinant leptin," Nature Genetics, vol. 12, pp. 318–320, Mar. 1996.

Griese, M., "Pulmonary surfactant in health and human lung diseases: state of the art," European Respiratory Journal, vol. 13, pp. 1455–1476, 1999.

Loffreda, S., et al., "Leptin regulates proinflammatory immune responses," The FASEB Journal, vol. 12, pp. 57–65, Jan. 1998.

Sierra–Honigmann, M., et al., "Biological action of leptin as an angiogenic factor," Science, vo. 281, pp. 1683–1686, Sep. 11, 1998.

* cited by examiner

SPA
C 1L 10L

SPB
C 1L 10L

SPC
C 1L 10L

GAPDH
C 1L 10L

METHOD FOR TREATING RESPIRATORY DISTRESS SYNDROME

BACKGROUND

I. Field of Invention

The present invention provides a new method for treating pulmonary distress caused by low or insufficient surfactant production in infants, children or adults. More particularly, the method of the invention utilizes leptin to treat individuals with impaired lung surfactant production and is particularly useful for treating Respiratory Distress Syndrome (RDS) in premature infants.

II. Backgroud of Invention

Premature infants are at increased risk for developing Respiratory Distress Syndrome (RDS), the leading cause of neonatal morbidity and mortality in developed countries (Mendelson et al., Bailliere's Clin. Endocrinol. Metab. 4:351–78, 1990). This condition is caused by a deficiency of lung surfactant, a complex material consisting of phospholipids, neutral lipids, carbohydrate and proteins. These infants require assisted ventilation and supplemental oxygen for prolonged periods of time. Often these infants develop Bronchopulmonary Dysplasia (BPD), a chronic lung disease associated with neurodevelopmental delay, poor growth, and late mortality (Bader et al., J. Pediatr. 110(5):693–9, 1987; Gibson et al., Am. J. Dis. Child. 143(7):721–5, 1988; Kurzner et al., Pediatrics 81(3):379–84, 1988; Vohr et al., Dev. Med. Child. Neurol. 33(8):690–7, 1991). Inflammation, primarily due to oxygen-induced free radical formation, positive pressure ventilation, and infection, is thought to be a key factor in the lung injury observed in these infants (Pierce and Bancalari, Pediatr. Pulmonol. 19(6):371–8, 1995).

Strategies aimed at treating the pulmonary inflammation in BPD through the use of systemic steroids have not shown a favorable outcome in decreasing the overall incidence of this disease. Three large multicenter trials, which enrolled a total of 1348 infants, independently showed no significant benefit to early administration (within 72 hours of life) of steroids on the incidence of BPD (Halliday et al., In: Hot Topics in Neonatology, Ross Laboratories, pp. 267–75, 1999; Soll et al., Pediatr. Res. 45: 226A, 1999; Stark et al., Pediatrics Supplement 104: 739A, 1999). Two of these trials were stopped prematurely due to concerns of significant detrimental side effects, including gastrointestinal perforation, periventricular leukomalacia, poor weight gain, gastrointestinal hemorrhage, and hypertension. Long term follow-up studies have shown a significant detrimental effect on somatic growth (Gibson et al., Arch. Dis. Child 69: 505–9, 1993, Yeh et al., Pediatrics 101(5):E7, 1998; O'Shea et al., Pediatrics 104(1 part 1):15–21, 1999). These adverse effects may be related to the catabolic effects of steroids on growing tissues (Tsai et al., Act. Paediatr. 85(12):1487–90, 1996). Efforts to reduce the incidence of BPD using other strategies such as inhaled steroids, high-frequency ventilation, and treatment of RDS with surfactant have also shown mixed results. There has been some success in reducing the incidence of RDS by enhancing surfactant production in utero via glucocorticoid administration to mothers in preterm labor (Liggins and Howie, Pediatrics 59:515–25, 1972). However, this treatment strategy is dependent on accurate identification of those mothers at risk for preterm delivery, and thus, is only effective for a small subset of premature infants affected with RDS. Furthermore, despite significant advances in neonatal care during the past three decades, the incidence of RDS and BPD has not changed significantly. There remains a clear need to identify alternative treatment strategies for this disease.

As more fully described below, the present invention overcomes the problems associated with previous forms of RDS therapy and includes a novel method of treating RDS that can be administered to premature infants as well as infants, children or adult subjects who have deficient lung surfactant.

SUMMARY OF THE INVENTION

The present invention includes a method for treating respiratory distress by treatment with leptin. According to the invention, leptin may be administered orally as well as by intravenously, intramuscularly, and other parenteral and enteral means. In one embodiment, the invention includes a method for treating RDS and BPD in premature infants. Another aspect of this invention is its usefulness for treating infants, children or adults suffering from pulmonary distress caused by low or insufficient production of surfactant. The present invention overcomes the problems associated with previous forms of RDS therapy, particularly the use of steroids.

The method of the invention provides for improving lung surfactant production in an individual with impaired surfactant production by administering a leptin compound to the individual for a time and in an amount sufficient to enhance surfactant production. The individual may be any mammal. Further, while the invention may be used for the treatment of any individual with impaired lung surfactant production, it is particularly useful for treating infants with intrauterine development of less than nine months. The leptin compound may comprise at least a biologically active fragment of leptin that is capable of binding to the leptin receptor and eliciting a biological effect such as increased surfactant production, and may be derived from any source of leptin or a biologically active fragment of leptin including recombinant protein.

In the method of the invention, the leptin compound is administered in a dosage from about 0.1 ng/kg body weight to about 100 mg/kg body weight and by a method selected from the group consisting of subcutaneously, intradermally, intravenously, intramuscularly, intraperitoneally, transdermally, orally, enteral tube feeding, pulmonary delivery, intranasal delivery, controlled release delivery and pump delivery.

Leptin may be administered with nutritional supplements, growth factors, and steroids, such as dexamethasone, that increase lung function. In a preferred embodiment, the growth factors may be selected from the group consisting of epidermal growth factor, fibroblast growth factor, insulin-like growth factor, thyroid hormone, and platelet derived growth factor.

Further, the method of the invention which comprises administering a leptin compound to an individual with impaired lung surfactant production for a time and in an amount sufficient to enhance surfactant production is particularly suitable for the treatment of individuals with Respiratory Distress Syndrome (RDS) and/or Bronchopulmonary Dysplasia (BPD). For treating RDS or BPD, the leptin compound comprises at least a biologically active fragment of leptin which is administered in a dosage from about 0.1 ng/kg body weight to about 100 mg/kg body weight. The leptin compound is administered by a method selected from the group consisting of subcutaneously, intradermally, intravenously, intramuscularly, intraperitoneally, transdermally, orally, enteral tube feeding, pulmonary delivery, intranasal delivery, controlled release delivery and pump delivery.

DETAILED DESCRIPTION OF THE INVENTION

Figure 1:
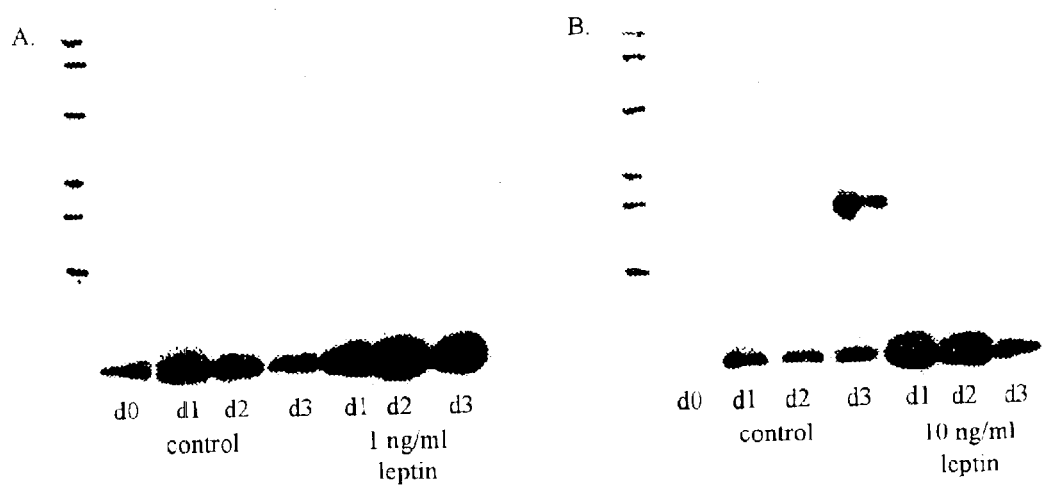
FIG. 1 is a Western blot analysis of SP-B (surfactant protein-B) from 21-day gestation, fetal rat lung explants cultured in the presence or absence of leptin. Fetal lung explants were exposed to either (A) 1 ng/ml or (B) 10 ng/ml leptin from initiation of culture (day 0). Explants were harvested and protein extracts were prepared on days (d) 1, 2, and 3 of culture. Western blots were probed with an antibody specific to rat SP-B.

The present invention includes a method for treating RDS by treatment with leptin. The invention is based on studies that show that leptin is produced by the placenta, that leptin levels in cord blood are correlated with newborn birth weights, that leptin is produced by the mammary gland and is found in breast milk, that leptin levels are higher in female as compared to male newborns, and that leptin augments surfactant production in fetal lung explant cultures. The combination of this role in fetal lung development with the known facts that the incidence of RDS mortality is lower in female as opposed to male infants and lower in breast-fed than in formula-fed infants points to an important role of leptin in maturation and function of the lung and forms the basis of the method of this invention.

Recent studies on the hormone leptin have outlined its role in energy homeostasis, regulating such diverse processes as satiety, fetal and neonatal growth, and immune function (reviewed in Campfield, Smith, and Burn, Science 280:1383–7, 1998). Leptin, a 167 amino acid cytokine hormone produced by the obesity (ob) gene, was initially thought to be adipocyte-specific (Zhang et al., Nature 372: 425–32, 1994). However, Hassink et al. (Pediatrics 100: e1–e6, 7, 1997) have discovered high level expression of leptin mRNA and protein in human placenta, and speculated that leptin was produced by the syncytiotrophoblasts. This was subsequently confirmed by Masuzaki et al. (Nat. Med. 3:1029–33, 1997). Additionally, leptin has been shown to be produced by gastric epithelium (Bado et al., J. Clin. Endo. Metab. 82: 1642–5, 1998) and the mammary gland (Smith-Kirwin et al., J. Clin. Endo. Metab. 83: 1810–3, 1998). Furthermore, under conditions of nutrient deprivation, leptin is also produced in skeletal muscle and induces its own expression in this tissue (Wang et al., Nature 393: 684–8, 1998; Nat. Med 5: 895–9, 1999).

Leptin regulates appetite and metabolic activity in mice (Rohner-Jeanreanaud and Jeanreanaud, N. Engl. J. Med. 344: 324–5, 1996) by acting through the long form of the leptin receptor (OB-Rb) in the hypothalamus (Campfield, Smith, and Burn, Science 280: 1383–7, 1998). Recently, additional roles for leptin have been suggested. Leptin has been demonstrated to have angiogenic activity in vivo and in vitro (Sierra-Honigmann et al., Science 281: 1683–6, 1988). These studies showed that leptin induces neovascularization in cornea from normal rats but not fa/fa Zucker rats, which lack a functional leptin receptor. In leptin-deficient (ob/ob) mice, puberty and pregnancy cannot be established without leptin administration (Chehab, Lim, and Lu, Nature Gen. 12: 318–20, 1996), indicating that leptin may have a role in sexual maturation and development (Hassink et al., Pediatrics 98: 201–5, 1996). Other roles for leptin include a regulator of hematopoeisis (Cioffi et al., Nature Medicine 2: 585–9, 1996; Gainsford et al., Proc. Natl. Acad. Sci. USA 93: 14564–8, 1996), glucose metabolism (Kamohara et al., Nature 389: 374–7, 1997), and proinflammatory immune responses (Loffreda et al., FASEB J. 12: 57–65, 1998; Lord et al., Nature 394: 897–901, 1998). Leptin-deficient ob/ob mice were also noted to have a specific respiratory phenotype of alveolar hyperventilation and chronic hypercapnia noted in age and weight-matched ob/ob mice before pronounced obesity. In a subsequent study, Tankersley et al. (J. Appl. Physiol. 85: 2261–9, 1998) demonstrated that leptin administration to ob/ob mice ameliorated the volume-dependent decrease in lung compliance in these animals. leptin has also recently been shown to prevent respiratory depression in ob/ob mice (O'Donnell et al., Am. J. Resp. Crit. Care Med. 159: 1477–84, 1999). Because these ob/ob mice were born to either wild type or ob/ob mothers, the fetuses were exposed to placental and possibly, maternal, leptin in utero. Thus, it was not possible to ascertain whether leptin affects fetal lung development in utero.

The observation that leptin is synthesized and secreted by human (Hassink et al., Pediatrics 100: e1–e6, 1997), rat (Chien et al., Biochem. Biophys. Commun. 237: 476–80, 1997) and mouse (Hoggard et al., Proc Nat Acad. Sci. 94: 1073–8, 1997) placental tissue has important implications, since it suggests a novel role for leptin in fetal growth and development. Because leptin expression was observed in human placenta from near-term pregnancies and in mouse placenta from 14.5 day but not from 12 day of gestation (Tomimatsui et al., Biochem. Biophys. Res. Comm. 240:213–5, 1997; Hoggard et al., Proc. Nat. Acad. Sci. 94:1073–8, 1997), it is suggested that leptin regulates some aspect of developmental growth in the fetus during the second half of gestation. In the human, leptin has been detected in cord blood as early as 18 weeks of gestation (Jaquet et al., J. Clin. Endo. Metab. 83:1243–6, 1998). Leptin levels in cord blood increase with gestation (Jaquet et al., J. Clin. Endo. Metab. 83:1243–6, 1998) and show a good correlation with the birth weight of the newborn (Hassink et al., Pediatrics 100:e1–e6, 1997; Matsuda et al., J. Clin. Endo. Metab. 82:16424, 1997), further supporting the hypothesis that leptin regulates fetal growth. Premature infants are delivered before the late pregnancy rise in leptin occurs (Masuzaki et al., Nat. Med. 3:1029–33, 1997) and have low cord blood leptin levels (Highman et al., Am. J. Obstet. Gynecol. 178:1010–5, 1998).

Without intending to be bound by theory, it is believed that leptin is important for lung growth and/or maturation and that the lack of leptin exposure late in pregnancy when the type II alveolar cells are maturing and producing surfactant could contribute to the respiratory distress suffered by many premature infants. Since leptin has been found in amniotic fluid, leptin may have a direct effect on type II alveolar cell maturation and growth, thereby increasing surfactant production.

The inadequacy and/or absence of pulmonary surfactant production at birth is one of the most serious and life threatening problems faced by the premature infant. Surfactant production is a maturation-dependent process, and deficiency results in RDS, which is characterized by inability to expand the alveoli and sustain adequate ventilation. Currently, treatment of RDS involves administering prenatal steroids to the mother in an attempt to increase surfactant production prior to delivery, administration of exogenous surfactant to the premature infant after birth, and supportive treatment with artificial ventilation until the premature infant's lungs mature. RDS accounts for a substantial burden of morbidity and mortality in premature infants, as well as significant emotional and financial burdens on the family. Although steroids increase serum leptin levels, there is recent evidence that glucocorticoids interfere with leptin's interaction with its receptor (Ur et al., Horm. Metab. Res. 28:4744–7, 1996; Zakrzewska et al., Diabetes 46:717–9, 1997). Furthermore, glucocorticoids may contribute to the development of central leptin resistance (Zakrzewska et al., Diabetes 46:717–9, 1997). These effects of glucocorticoids may contribute to the poor growth observed in premature infants treated with steroids. Therefore, it is desirable to provide a method for treating RDS that does not involve the use of steroids.

The method of the present invention, which consists of administration of a leptin compound to a patient, avoids the use of steroids while providing effective treatment for premature infants who suffer from conditions in which there is insufficient production of surfactant. The method is also effective for treatment of newborns, infants, children, and adults who suffer from any condition caused by insufficient surfactant production as administration of the leptin compound is expected to increase surfactant production and improve lung function.

More particularly, the present invention provides a method for restoring pulmonary function in a patient who suffers from a lung disease characterized by insufficient surfactant production. Abnormalities of surfactant production have been described in obstructive lung diseases, such as asthma, bronchitis, chronic obstructive pulmonary disease, and following lung transplantation (reviewed in Grise, Eur. Resp. J. 13(6): 1455–76, 1999). Abnormal surfactant production has also been seen in infectious and suppurative lung diseases, such as cystic fibrosis, pneumonia, and AIDS. Finally, insufficient surfactant also characterizes diseases such as acute respiratory distress syndrome (ARDS), pulmonary edema, interstitial lung diseases, pulmonary alveolar proteinosis, following cardiopulmonary bypass, and in smokers. The method comprises administering a leptin compound to the host for a time and in an amount sufficient to restore or enhance respiratory function. Typically, the leptin compound will be administered in a dosage from about 0.1 ng per kg body weight to about 100 mg per kg body weight, for example. Effective amounts are determined by such factors as the leptin composition, the mode of administration, the weight and general health of the patient, and the judgment of the prescribing physician, for example. Considerations associated with such factors are well known by those persons skilled in the art.

Further, the present invention, which has been discussed in the context of human patients, is not limited to use in humans, but is also effective in treating respiratory conditions caused by inadequate surfactant production in other mammalian species.

In the treatment of premature infants, the leptin compound is typically administered to any premature infant at increased risk of developing RDS from the onset of birth to the time when the infant would have reached full gestational age. For example, an infant born 4 months prematurely is typically treated with leptin for 4 months or until lung function is restored. For individuals that develop respiratory distress after birth, the individual is treated with leptin for a period of time until lung function is restored, as ascertained by clinical measurements that are known to those skilled in the art.

The leptin compound may be administered subcutaneously, intradermally, intravenously, intramuscularly, intraperitoneally, via enteral tube feeding, via pulmonary delivery, via intranasal delivery, transdermally, orally, via controlled release, via pump, or by any other conventional route of administration for polypeptide drugs. Typically, the leptin compound will be administered continuously during the period of administration, i.e., being delivered at least once per day or via controlled release techniques, such as via transdermal patches or leptin in milk fat globules. Furthermore, leptin may be administered antenatally to those mothers at increased risk of delivering prematurely. Leptin may also be administered antenatally with glucocorticoids. The administration of leptin has been described in U.S. patent application Ser. No. 09/302,117 which is incorporated herein by reference in its entirety.

Leptin may be derived from any mammal. Preferably human leptin is used for the treatment of humans. A leptin compound may include, but is not limited to, either the full active peptide or a biologically active fragment that is capable of binding to the leptin receptor and eliciting a biological effect such as increased surfactant production. Methods for purification of leptin, production of the recombinant form, and active biological fragments have been described in U.S. Pat. Nos. 5,552,524; 5,552,523; 5,552522; 5,521,283; 5,5908,830, incorporated herein by reference in their entireties.

In some embodiments, the invention provides compositions for administration which comprises a solution of leptin dissolved or suspended in an acceptable carrier, preferably an aqueous carrier. A variety of aqueous carriers may be used, e.g., water, buffered water, 0.8% saline, 0.3% glycine, hyaluronic acid and the like. These compositions may be sterilized by conventional, well-known sterilization techniques, or may be filter-sterilized. The resulting aqueous solutions may be packaged for use as is, or lyophilized, the lyophilized preparation being combined with a sterile solution prior to administration. The compositions may contain pharmaceutically acceptable auxiliary substances as required to approximate physiological conditions, such as pH adjustments and buffering agents, adjusting agents, wetting agents and the like, for example, sodium acetate, sodium lactate, sodium chloride, potassium chloride, calcium chloride, sorbitan monolaurate, triethanolamine oleate, etc.

The concentration of leptin in the pharmaceutical formulations can vary widely, i.e., from less than about 0.1% to as much as 20% to 50% or more by weight, and will be selected primarily by fluid volumes, viscosities, etc., in accordance with a particular mode of administration selected. A value of about 2% is common for many formulations, for example.

For solid compositions, conventional nontoxic solid carriers may be used which include for example, pharmaceutical grades of mannitol, lactose, starch, magnesium sterate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10% to 95% of active ingredient, that is one or more leptin compounds of the invention, and more preferably at a concentration of 25% to 75%.

For aerosol administration, leptin is preferably supplied in finely divided form along with an aerosol surfactant and propellant. Typical percentages of leptin are 0.01% to 20% by weight preferably 1%–10%. The aerosol surfactant must, of course be nontoxic, and preferably suitable to the propellant. Representative of such agents are the esters or partial esters of fatty acids containing from 6 to 22 carbon atoms such as caproic, octanoic, lauric, palmatic, stearic linoleic, linolenic, olesteric and oleic acids with an aliphatic polyhydric alcohol or its cyclic anhydride. Mixed esters, such as mixed or natural glycerides may be employed. The aerosol surfactant may constitute 0.1% to 20% by weight of the composition, preferably 0.25–5%. The balance of the composition is ordinarily propellant. A carrier can also be included, as desired, as with, e.g., lecithin for intranasal delivery.

The leptin compositions of the invention can additionally be delivered in a controlled release system encapsulated form, or an implant by techniques well known in the art. The compositions of the invention can also be delivered via a pump, such as a minipump, or by administration of milk fat globules containing leptin as disclosed in co-pending U.S. patent application Ser. No. 09/302,117.

EXAMPLES

1. Effects of Leptin on Surfactant Production in the Fetal Lung Explant Model

We have used a fetal lung explant model to mimic the conditions of the premature lung. Lungs from d21 rat fetuses, term being 22 days, were dissected free of heart, trachea and bronchi and placed in ice-cold serum free Waymouth medium and cut into 1 mm$^3$ pieces on a McIlwain tissue chopper. The lung explants were placed in tissue culture dishes that were scratched (along each half) to facilitate attachment of explants. The excess medium was aspirated and fresh medium (2 ml for 60 mm plate) was gently placed on the explants. The 17–21 d explants were incubated in 95% $O_2$–5% $CO_2$, since incubation of these explants in 5% $CO_2$ in air can cause compression of airways (Gross and Wilson, J. Appl. Physiol. 55: 1725–32, 1983). The petri dishes were placed on a tilting platform and allowed to rest for 90 min in a humidified atmosphere in a $CO_2$ incubator. Thereafter, the plates were tilted at 34 cycles per minute so that during each cycle, one half of the petri dish was exposed to gas phase and the other half was covered with the medium. Leptin at either 1 or 10 ng/ml was added to the explant cultures on the day of establishment of the culture (day 0). The explants were cultured for varying periods of time for up to 3 days, and protein extracts were prepared to establish a time course for leptin effects on the fetal lung. Surfactant proteins were separated by electrophoresis on 15% polyacrylamide—SDS gels, and transferred to nitrocellulose membranes by electroblotting. The membranes were blocked with 2% gelatin (BioRad), treated overnight with anti-SP-B, and then with secondary antibody (goat anti-rabbit HRP-conjugated antibody). The blots were then reacted with a chemiluminescent substrate solution (SuperSignalR, Pierce Chemical Co.) and exposed to X-ray films to detect proteins that are recognized by the primary antibody. A set of known concentrations of protein was run in parallel to ascertain that the amount of sample protein is within the linear range of density.

FIG. 1 shows that 1 ng/ml leptin increases SP-B production above that of the control cultures after either 48 or 72 h of leptin exposure. A higher concentration of leptin (10 ng/ml) increases SP-B production after 24 h, but decreases SP-B levels after 48 and 72 h.

To explore the effect of gestational age on surfactant production in response to leptin, we exposed younger lung explant cultures (d17) to 1 ng/ml leptin. Total RNA was extracted by homogenizing the explants in 4M guanidine thiocyanate, applying the lysate on a Qiagen RNeasy column (Qiagen, Chatsworth, Calif.), and recovering total RNA according to the manufacturer's instructions. RNA was quantified by measurement of absorbancy at 260 nm ($A_{260}$). The quality of RNA was assessed by the $A_{260}/A_{280}$ ratio and by separation on agarose gels. Total RNA (1 µg) was brought up to 10 µl in DEPC-treated water. The sample was heated to 75° C. for 3 min, placed on ice, and cDNA synthesis was performed by reverse transcription for 15 min at 42° C. in a 20 µl reaction containing 1×PCR buffer II (Perkin-Elmer), 5 mM $MgCl_2$, 1.25 mM each dNTP, 1 U/µl RNasin (Promega), 12.5 µg/µl oligo (dT) 15, and 2.5 U/µl AMV reverse transcriptase (Promega Madison, Wis.). Subsequent amplification of the cDNA sequence was performed with 10 µl of the reverse transcription reaction in 1×Taq buffer, 5% DMSO, 25 pmol each primer (Table 1), and 1.25 U Taq polymerase in a 50 µl reaction volume.

TABLE 1

Sequence of PCR primers used in the RT/PCR experiments

| Primer | Gene | Sequence |
|--------|------|----------|
| RSPAF | Rat SP-A | 5'CCTCTTCTTGACTGTTGTCGCTGG3' (SEQ. ID. NO. 1) |
| RSPAR | Rat SP-A | 5'GCTGAGGACTCCCATTGTTTGCAG3' (SEQ. ID. NO. 2) |
| RSPBF | Rat SP-B | 5'GGAGCTAATGACCTGTGCCAAGAG3' (SEQ. ID. NO. 3) |
| RSPBR | Rat SP-B | 5'CTGGCCCTGGAAGTAGTCGATAAC3' (SEQ. ID. NO. 4) |

TABLE 1-continued

Sequence of PCR primers used in the RT/PCR experiments

| Primer | Gene | Sequence |
|---|---|---|
| RSPBR2 | Rat SP-B | 5'AAGTACTGTGTAACGCTCAGCCAG3' (SEQ. ID. NO. 5) |
| RSPCF | Rat SP-C | 5'GATGGAGAGCCCACCGGATTACTC3' (SEQ. ID. NO. 6) |
| RSPCR | Rat SP-C | 5'GAACGATGCCAGTGGAGCCAATAG (SEQ. ID. NO. 7) |
| ROBRaF | Rat OB-Ra | 5'AGTGAATGCTGTGCAGTCACTCAG3' (SEQ. ID. NO. 8) |
| ROBRaR | Rat OB-Ra | 5'CAAAGAGTGTCCGCTCTCTTTTGG3' (SEQ. ID. NO. 9) |
| ROBRbF | Rat OB-Rb | 5'GGATGAGTGTCAGAGTCAACCCTC3' (SEQ. ID. NO. 10) |
| ROBRbR | Rat OB-Rb | 5'CAGTTCCAAAAGCTCATCCAACCC3' (SEQ. ID. NO. 11) |
| ACTF1 | Rat β-actin | 5'TGTATGCCTCTGGTCGTACCAC3' (SEQ. ID. NO. 12) |
| ACTR1 | Rat β-actin | 5'ACAGAGTACTTGCGCTCAGGAG3' (SEQ. ID. NO. 13) |
| GAPDHF | Rat GAPDH | 5'GGTCGGTGTCAACGGATTTG3' (SEQ. ID. NO. 14) |
| GAPDHR | Rat GAPDH | 5'GAGATGATGACCCTTTTGGC3' (SEQ. ID. NO. 15) |

For assessment of the relative levels of SP-A, SP-B and SP-C transcripts, a multiplex RT/PCR reaction with β-actin was used. The temperature profile for the PCR reactions consisted of a 2 min melting step at 95° C., then 30 cycles of 30 s at 94° C., 30 s at 55° C., and 60 sec at 65° C., followed by a final extension step of 5 min at 72° C. RT-PCR products were separated by size on a 4% agarose gel and stained with ethidium bromide. Gel visualization and quantitative analysis of relative band intensities was performed using Eagle Eye II hardware and software (Stratagene, La Jolla, Calif.).

Figure 2:
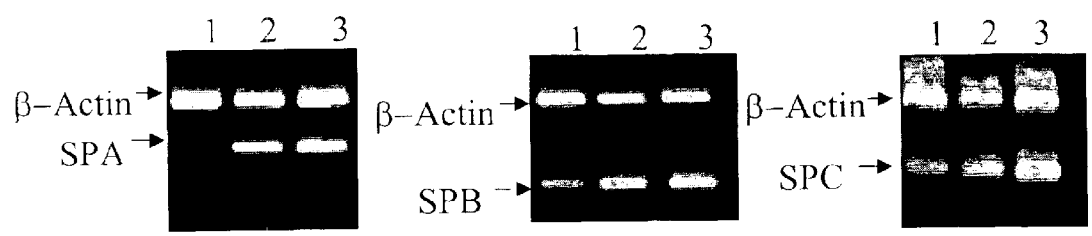
FIG. 2 shows RT-PCR analysis of surfactant protein A (SP-A), surfactant protein B (SP-B), surfactant protein C(SP-C), and β-actin mRNA expression in day 17 fetal lung explant cultures. Cultures were exposed to 1 ng/ml leptin (lanes 3, A-C) or control medium (lanes 2, A-C), and total RNA was isolated at the indicated day of culture. Total RNA was reverse transcribed and amplified with both β-actin and leptin PCR primers. In each figure, lane 1 is the time of initiation of culture (day 0). Low levels of all surfactant RNAs were detected in the uncultured cells (lanes 1, A-C). The size of the β-actin RT/PCR product is 492 bp; the size of SP-A is 352 bp; SP-B is 201 bp, and SP-C is 284 bp.
Figure 3:
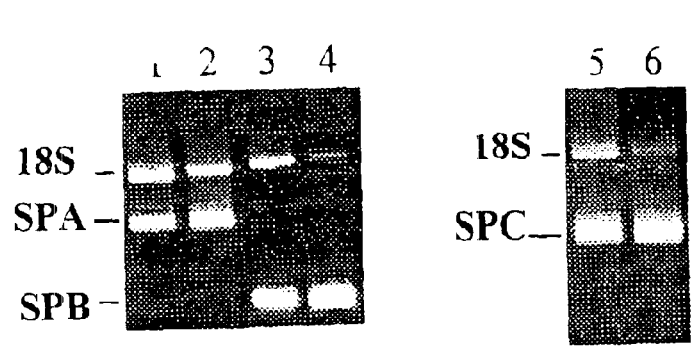
FIG. 3 shows RT-PCR results of an experiment that determines the relative levels of the surfactant mRNAs to that of 18S rRNA in day 17 fetal lung explants. Qualitative RT/PCR detection of surfactant mRNA was performed using the Ambion QuantumRNA kit (Ambion, Austin, Tex.) and 1 µg of total RNA isolated from explants cultured for 3 days in culture. Lanes 1, 3,5: control day 3; lanes 2, 4, 6: 1 ng/ml leptin day 3.

FIG. 2 shows that leptin significantly increases SP-A and SP-C mRNA levels. However, leptin also increases the levels of β-actin in fetal lung explant cultures. This results in an underestimation of the actual increase in surfactant mRNA levels. Therefore, we chose to use 18S rRNA to determine the relative levels of surfactant mRNA because of the invariant expression of 18S rRNA across tissues and treatments. Since 18S rRNA is much more abundant than any mRNA species, modified 18S rRNA primers called competimers (Ambion) are used that cannot be extended by Taq polymerase. By adjusting the ratio of competimers to normal 18S rRNA primers, the RT/PCR signal for 18S rRNA can be decreased to the level of even rare messages, as described by the manufacturer. FIG. 3 shows the results of such an experiment for determining the relative levels of the surfactant mRNAs to 18S rRNA. FIG. 3 shows that leptin increases the mRNA levels for SP-A, SP-B, and SP-C relative to the levels of 18S rRNA by 1.6-, 5-, and 2-fold, respectively, in d17 lung explant cultures after 3 days in culture. These experiments support the hypothesis that leptin has an effect on the maturation of type II alveolar cells.

2. Changes in Leptin Receptor Gene Expression in Relation to Lung Maturation

Figure 4:
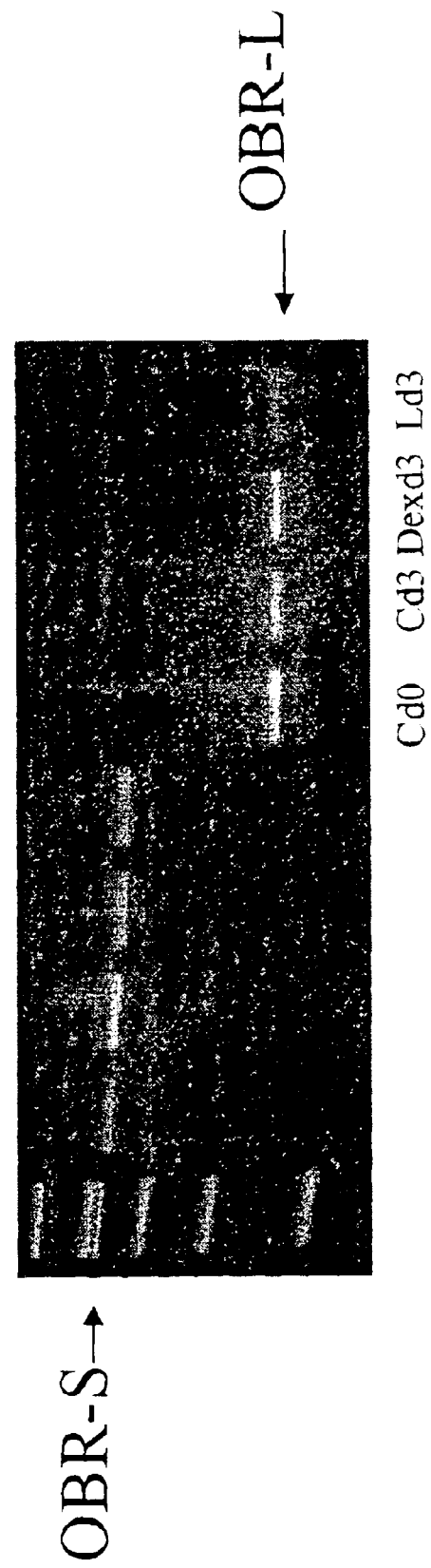
FIG. 4 depicts RT-PCR analysis of leptin receptor expression in day 17 fetal lung explant cultures. Total RNA was reverse transcribed and amplified with either the short (OB-Ra) or the long (OB-Rb) form of the leptin receptor. Day 0 (Cd0) represents the time of initiation of culture. The fetal lung explants were exposed for 3 days to either control medium (Cd3), 1 ng/ml leptin (Ld3), or 10 nM dexamethasone (Dexd3). The size of the OB-Ra RT/PCR product is 479 bp and OB-Rb is 262 bp.

Both the long (OB-Rb) and short (OB-Ra) forms of the leptin receptor are expressed in fetal lung explant cultures (FIG. 4). As the fetal lung cells mature in culture, the expression of OB-Ra mRNA increases, whereas OB-Rb mRNA levels decrease. Leptin administration similarly decreases expression of OB-Rb mRNA, whereas dexamethasone increases OB-Rb mRNA levels in fetal lung explants (FIG. 4). Taken together, these data demonstrate the presence of OB-Ra and OB-Rb mRNA in rat fetal explant lung cultures. As type II alveolar cells mature in culture, mRNA levels of OB-Ra increase and OB-Rb decrease; leptin administration further decreases OB-Rb mRNA levels, whereas dexamethasone increases OB-Rb mRNA expression.

3. Leptin Increases mRNA Levels of Surfactant Proteins in Isolated Fetal Alveolar Type II Cells To determine if the leptin effect on surfactant production was due to a direct effect of leptin on the type II alveolar cell, we determined whether the effects of leptin could be reproduced in isolated type II alveolar cells in culture. Alveolar type II cells were obtained from the lungs of 19-d gestation fetal rats by the method described by Bhandari et al., (Pediatr. Res. 41:166–71, 1997). In brief, lungs of 19-day gestation fetal rats were removed, dissected free of connective tissue and nonparenchymal pulmonary tissue, and cultured as explants for 40–48 h in serum free Waymouth MB 752/1 medium with penicillin and streptomycin in humidified 95% $O_2$/5% $CO_2$ at 37° C. During this time, endothelial and blood cells do not survive, which is a crucial step in the enrichment of primary cultures of Type II cells from fetal lung. The explant cells were then harvested and the cells dissociated using a solution of collagenase, trypsin and DNase. The mixed cell suspension was subjected to three differential adhesions to remove fibroblasts. The nonadherent suspension containing an enriched population of fetal type II cells was plated at $2 \times 10^6$ cells/35 mm dish in 2 ml of minimum essential medium containing penicillin (100 U/ml), kanamycin (100 g/ml) and 2% fetal bovine serum. The cells were cultured for 20–22 h at 37° C. in 5 % $CO_2$/room air (Bhandari et al., Pediatr. Res. 41:166–71, 1997). Cultures contain 90–95% type II cells of which >99% are viable as determined by exclusion of the vital dye, trypan blue. The usual yield of type II cells from the lungs of the fetuses (10–16) per pregnant rat is approximately $10^7$ cells.

Figure 5:
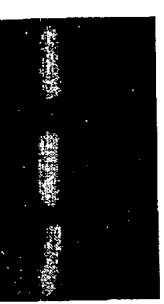
FIG. 5 depicts RT-PCR analysis of surfactant and GADPH (glyceraldehyde phosphate dehydrogenase) mRNA expression in cultured isolated type II alveolar cells. Cells were exposed to either 1 ng/ml leptin (1 L) or 10 ng/ml leptin (10 L). Control cells were not exposed to leptin.
Figure 5:
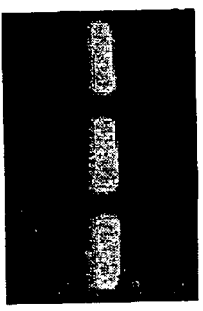
Figure 5:
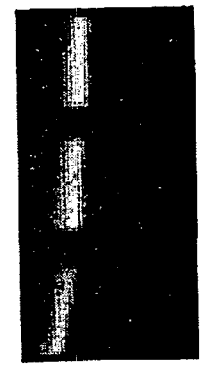

Type II cells from d19 fetal lungs were cultured for 24 h and then exposed to either 1 or 10 ng/ml leptin for 24 h. Total RNA was isolated from these cells and then examined for SP-A, SP-B, SP-C, and GAPDH (housekeeping gene) mRNA expression. FIG. 5 shows that a 24 h treatment with 1 ng/ml leptin increased SP-A, SP-B, and SP-C, but not GAPDH, mRNA levels after 24 h. These data suggest that leptin acts directly on the type II cell and that the effects of leptin on SP-A, SP-B, and SP-C mRNA levels are most likely exerted at the transcriptional level.

Taken together, these data demonstrate that leptin administration both in fetal lung explant cultures and isolated type II alveolar cultures results in increases in SP-A, SP-B, and SP-C mRNA. Lung explants from day 21 fetuses produced increased surfactant proteins with leptin administration, possibly indicating an effect on maturation of type II alveolar cells. Thus, leptin provides a means to increase surfactant production in immature lungs, ultimately resulting in an additional treatment modality for premature infants with RDS and for other conditions characterized by insufficient surfactant production.

4. Antenatal Treatment of Pregnant Rats with Leptin

Leptin (1 mg/kg body weight) was administered to pregnant rats at d16 of gestation and 24 h later by intraperitoneal injection. Dexamethasone at 6 mg per kg body weight was administered at similar time intervals as leptin. In addition, the effect of a combination of leptin and dexamethasone treatment was tested. After 48 h of leptin, dexamethasone or leptin/dexamethasone exposure, premature delivery of the rat pups was induced at d18, which is similar to 30 weeks of gestation in the human. The fetuses from each litter were pooled and weighed, and various tissues from both the rat fetuses and mothers were also dissected and weighed. Table 2 shows that antenatal treatment with leptin increased the average weight of the fetal lungs in relation to their body weight by 51%. Antenatal treatment with dexamethasone increased fetal lung weight by 41%. Interestingly, combined therapy with leptin and dexamethasone increased fetal lung weight by 62%.

TABLE 2

Effect of antenatal treatment with dexamethasone, leptin, or dexamethasone and leptin on weight of maternal and fetal lungs

|  | Control | Dexa-methasone | Leptin | Dex + Leptin |
|---|---|---|---|---|
| Maternal lung weight (g) | 1.07 | 0.99 | 1.21 | 1.16 |
| Average weight fetal lungs (g) | 0.61 (n = 9) | 0.79 (n = 9) | 0.87 (n = 9) | 0.95 (n = 9) |
| Average weight fetal head (g) | 0.47 (n = 9) | 0.43 (n = 9) | 0.45 (n = 9) | 0.47 (n = 9) |
| Average weight fetus (g) | 1.64 (n = 9) | 1.52 (n = 9) | 1.56 (n = 9) | 1.59 (n = 9) |
| Weight fetal lung (g)/g fetus | 0.37 | 0.52 | 0.56 | 0.60 |

Figure 6:
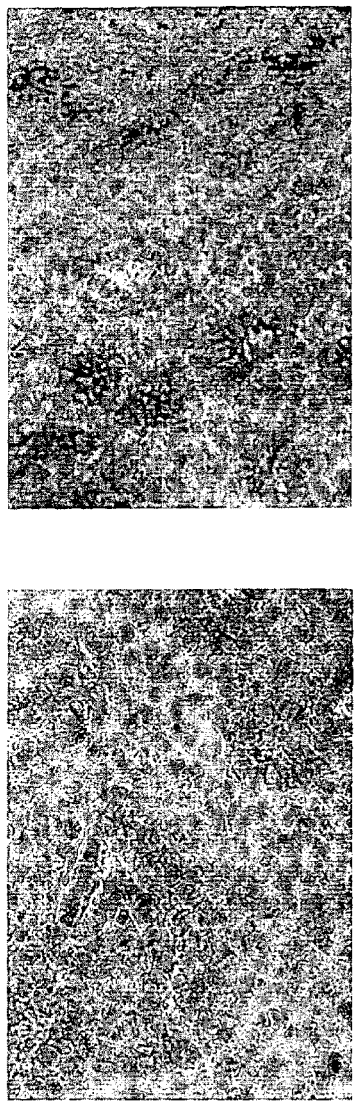
FIG. 6 depicts the effect of antenatal treatment with leptin or dexamethasone on fetal lung morphology. Fetal lung sections were stained with a histochemical stain for alkaline phosphatase, which identifies type II cells. Control, no leptin; dexamethasone (6 mg/ml for 48 h); leptin (0.25 mg/ml for 48 h).
Figure 6:
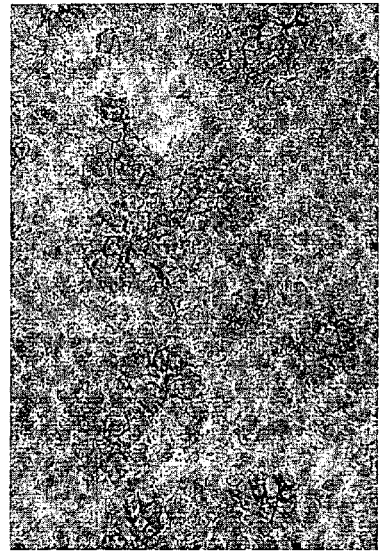

Histologic analysis of the lung tissue was done to determine the basis for the increased fetal lung weight. Type II cells were identified by alkaline phosphatase staining as previously described (Post and Smith, Am. Rev. Respir. Dis. 137: 525–30, 1988). Unfixed frozen 5 μm sections of fetal lung tissue were stained histochemically with alkaline phosphatase at pH 8.74 to identify type II alveolar cells. Slides were incubated for 60 minutes at 37° C. in 25 ml of 0.2M Tris-HCl buffer and 25 ml of deionized water, 5 mg of Naphthol AS-BI phosphate, 0.1 ml dimethylformamide, and 30 mg of fast red TR. The slides were then rinsed in 3 changes of deionized water, counterstained for 30 seconds in Harris hematoxylin and blued in running water for 3–5 minutes. Slides were mounted from water in Advantage™. The histologic analysis revealed that the increase in fetal lung weight in both the leptin- and dexamethasone-treated rats was paralleled by an increase in the number of type II alveolar cells (FIG. 6).

It will be readily understood by those persons skilled in the art that the present invention is susceptible to broad utility and application. Many embodiments and adaptations of the present invention other than those herein described, as well as many variations, modifications and equivalent arrangements, will be apparent from or reasonably suggested by the present invention and foregoing description thereof, without departing from the substance or scope of the invention.

Accordingly, while the present invention has been described here in detail in relation to its preferred embodiment, it is to be understood that this disclosure is only illustrative and exemplary of the present invention and is made merely for the purposes of providing full and enabling disclosure of the invention. The foregoing disclosure is not intended to be construed or to limit the present invention or otherwise to exclude any other such embodiments, adaptations, variations, modifications and equivalent arrangements, the present invention being limited by the claims and the equivalents thereof.

What is claimed is:

1. A method for improving lung surfactant production in an individual with impaired surfactant production, the method comprising administering a leptin or a biologically active fragment of leptin to the individual for a time and in an amount sufficient to enhance surfactant production.

2. The method of claim 1, wherein the individual is a mammal.

3. The method of claim 1, wherein the individual is an infant with an in utero development of less than nine months.

4. The method of claim 1, wherein the leptin or a biologically active fragment thereof is a recombinant protein comprising at least a biologically active fragment of leptin.

5. The method of claim 1, wherein the leptin or a biologically active fragment thereof is administered in a dosage from about 10 ng/kg body weight to about 100 mg/kg body weight.

6. The method of claim 1 wherein the step of administering the leptin or a biologically active fragment thereof includes administering to the individual milk fat globules containing leptin.

7. A method for improving lung surfactant production in an individual with respiratory distress syndrome, the method comprising administering leptin or a biologically active fragment thereof to the individual for a tine and in an amount sufficient to enhance surfactant production.

8. The method of claim 7, wherein the leptin or a biologically active fragment thereof is administered in a dosage from about 10 ng/kg body weight to about 100 mg/kg body weight.

9. The method of claim 7 wherein the step of administering the leptin or a biologically active fragment thereof includes administering to the individual milk fat globules containing leptin.

10. A method for improving lung surfactant production in an individual with Bronchopulmonary Dysplasia, the method comprising administering leptin or a biologically active fragment thereof to the individual for a time and in an amount sufficient to enhance surfactant production.

11. The method of claim 10 wherein the step of administering the leptin or a biologically active fragment thereof includes administering to the individual milk fat globules containing leptin.

* * * * *

SEQUENCE LISTING

```
<160> NUMBER OF SEQ ID NOS: 15

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 1
cctcttcttg actgttgtcg ctgg                                          24

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 2
gctgaggact cccattgttt gcag                                          24

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 3
```

-continued ggagctaatg acctgtgcca agag                                              24

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 4
ctggccctgg aagtagtcga taac                                              24

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 5
aagtactgtg taacgctcag ccag                                              24

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 6
gatggagagc ccaccggatt actc                                              24

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 7
gaacgatgcc agtggagcca atag                                              24

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 8
agtgaatgct gtgcagtcac tcag                                              24

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 9
caaagagtgt ccgctctctt ttgg                                              24

<210> SEQ ID NO 10
<211> LENGTH: 24
<212> TYPE: DNA

```
<213> ORGANISM: Artificial Sequence
<220> FEATURE:
<223> OTHER INFORMATION: Description of Artificial Sequence: Primer

<400> SEQUENCE: 10
ggatgagtgt cagagtcaac cctc                                              24

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 11
cagttccaaa agctcatcca accc                                              24

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 12
tgtatgcctc tggtcgtacc ac                                                22

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 13
acagagtact tgcgctcagg ag                                                22

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 14
ggtcggtgtc aacggatttg                                                   20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 15
gagatgatga ccctttttggc                                                  20
```